(12) United States Patent
McNulty et al.

(10) Patent No.: US 11,376,164 B2
(45) Date of Patent: Jul. 5, 2022

(54) NEGATIVE PRESSURE WOUND THERAPY ARTICLE WITH FEATURES

(71) Applicant: 3M INNOVATIVE PROPERTIES COMPANY, St. Paul, MN (US)

(72) Inventors: Amy K. McNulty, Stillwater, MN (US); Robert T. Fitzsimons, Jr., Minneapolis, MN (US); Kurt J. Halverson, Lake Elmo, MN (US); Bryan A. Baker, Minneapolis, MN (US); Jana Ninkovic, St. Paul, MN (US); Jie Liu, Woodbury, MN (US); Minghua Dai, Plymouth, MN (US); Wei Zhang, Woodbury, MN (US); Kiu-Yuen Tse, Woodbury, MN (US); David R. Holm, Hudson, WI (US); Graham M. Clarke, Woodbury, MN (US); Federica Sgolastra, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 51 days.

(21) Appl. No.: 16/770,989

(22) PCT Filed: Dec. 12, 2018

(86) PCT No.: PCT/IB2018/059972
§ 371 (c)(1),
(2) Date: Jun. 9, 2020

(87) PCT Pub. No.: WO2019/116279
PCT Pub. Date: Jun. 20, 2019

(65) Prior Publication Data
US 2020/0368072 A1    Nov. 26, 2020

Related U.S. Application Data

(60) Provisional application No. 62/598,674, filed on Dec. 14, 2017.

(51) Int. Cl.
*A61F 13/02* (2006.01)
*A61F 13/00* (2006.01)
(Continued)

(52) U.S. Cl.
CPC .... *A61F 13/0216* (2013.01); *A61F 13/00068* (2013.01); *A61F 13/022* (2013.01);
(Continued)

(58) Field of Classification Search
CPC .......... A61F 13/00017; A61F 13/00068; A61F 13/0206; A61F 13/0216;
(Continued)

(56) References Cited

U.S. PATENT DOCUMENTS 3,389,827 A   6/1968 Re
3,645,835 A   2/1972 Hodgson
(Continued)

FOREIGN PATENT DOCUMENTS

WO   WO 2010-056541   5/2010
WO   WO 2010-056543   5/2010
(Continued)

OTHER PUBLICATIONS

International Search Report for PCT International Application No. PCT/IB2018/059972, dated Mar. 14, 2019, 5 pages.

*Primary Examiner* — Susan S Su
*Assistant Examiner* — Eric Rassavong
(74) *Attorney, Agent, or Firm* — Qiang Han

(57) ABSTRACT

An article, including a network of interconnected polymeric strands; wherein each of the interconnected polymeric strands has a first surface adapted to contact a tissue site and a second surface opposite the first surface; wherein at least one of the interconnected polymeric stand has a plurality of features extending from the first surface of the interconnected polymeric strands; wherein at least one of the inter-
(Continued)

connected polymeric strands is non-linear; a plurality of openings between adjacent interconnected polymeric strands; an adhesive layer in contact with the second surface of the interconnected polymeric strands; and a filler in contact with the adhesive layer, the adhesive layer in between the network of interconnected polymeric strands and the filler; wherein the article is a negative pressure wound therapy article.

20 Claims, 3 Drawing Sheets

(51) Int. Cl.
  *A61L 15/22* (2006.01)
  *A61L 15/42* (2006.01)
(52) U.S. Cl.
  CPC .......... *A61F 13/0246* (2013.01); *A61L 15/22* (2013.01); *A61L 15/425* (2013.01); *A61F 2013/00174* (2013.01)
(58) Field of Classification Search
  CPC ........ A61F 2013/00119; A61F 13/0246; A61F 13/0233; A61F 13/02; A61M 1/962
  See application file for complete search history.

(56) References Cited

U.S. PATENT DOCUMENTS

| | | |
|---|---|---|
| 4,112,213 A | 9/1978 | Waldman |
| 4,310,509 A | 1/1982 | Berglund |
| 4,323,557 A | 4/1982 | Rosso |
| 4,595,001 A | 6/1986 | Potter |
| 4,737,410 A | 4/1988 | Kantner |
| 5,088,483 A | 2/1992 | Heinecke |
| 5,160,315 A | 11/1992 | Heinecke |
| 6,994,904 B2 | 2/2006 | Joseph |
| 7,494,482 B2 | 2/2009 | Orgill |
| 8,057,447 B2* | 11/2011 | Olson ................. A61F 13/0203 604/313 |
| 2010/0160876 A1 | 6/2010 | Robinson |
| 2013/0165836 A1* | 6/2013 | Locke ..................... A61L 15/42 602/44 |
| 2014/0234606 A1 | 8/2014 | Ausen |
| 2014/0296804 A1 | 10/2014 | Hicks |
| 2016/0074552 A1 | 3/2016 | Liu |
| 2017/0007462 A1 | 1/2017 | Hartwell |

FOREIGN PATENT DOCUMENTS

| | | | | |
|---|---|---|---|---|
| WO | WO-2014028470 A1 * | 2/2014 | ........... | B29C 43/222 |
| WO | WO 2014-149718 | 9/2014 | | |
| WO | WO-2015179235 A1 * | 11/2015 | ......... | A61L 26/0061 |
| WO | WO 2018-005275 | 1/2018 | | |

* cited by examiner

NEGATIVE PRESSURE WOUND THERAPY ARTICLE WITH FEATURES

BACKGROUND

Clinical studies and practice have shown that providing a negative pressure in proximity to a tissue site promotes the growth of new tissues at the tissue site. The application of negative pressure is successful in treating wounds. This treatment (frequently referred to in the medical community as "negative pressure wound therapy (NPWT)," "reduced pressure therapy," or "vacuum therapy") provides a number of benefits, including faster healing and increased formulation of granulation tissue. Typically, reduced pressure is applied to tissues through a foam, a pad or other manifolding device, such as gauze. The manifolding device typically contains cells, pores or other openings that are capable of distributing reduced pressure to the tissue and channeling fluids that are drawn from the tissue. The porous pad often is incorporated into a dressing having other components that facilitate treatment.

Other know NPWT articles are discussed in U.S. Pat. Nos. 7,494,482; 8,057,447; 8,889,243 and 9,107,989.

SUMMARY

In one aspect, the present disclosure provides an article, including a network of interconnected polymeric strands; wherein each of the interconnected polymeric strands has a first surface adapted to contact a tissue site and a second surface opposite the first surface; wherein at least one of the interconnected polymeric strands has a plurality of features extending from the first surface of the interconnected polymeric strands; wherein at least one of the interconnected polymeric strands is non-linear; a plurality of openings between adjacent interconnected polymeric strands; an adhesive layer in contact with the second surface of the interconnected polymeric strands; and a filler in contact with the adhesive layer, the adhesive layer in between the network of interconnected polymeric strands and the filler; wherein the article is a negative pressure wound therapy article.

In another aspect, the present disclosure provides a system, including the article of present disclosure and a reduced pressure source connected to article to deliver the reduced pressure through the opening, between the features, and to the tissue site.

In another aspect, the present disclosure provides a method, including providing the article of present disclosure and positioning the article on a wound.

Various aspects and advantages of exemplary embodiments of the present disclosure have been summarized. The above Summary is not intended to describe each illustrated embodiment or every implementation of the present disclosure. Further features and advantages are disclosed in the embodiments that follow. The Drawings and the Detailed Description that follow more particularly exemplify certain embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

Figure 1:
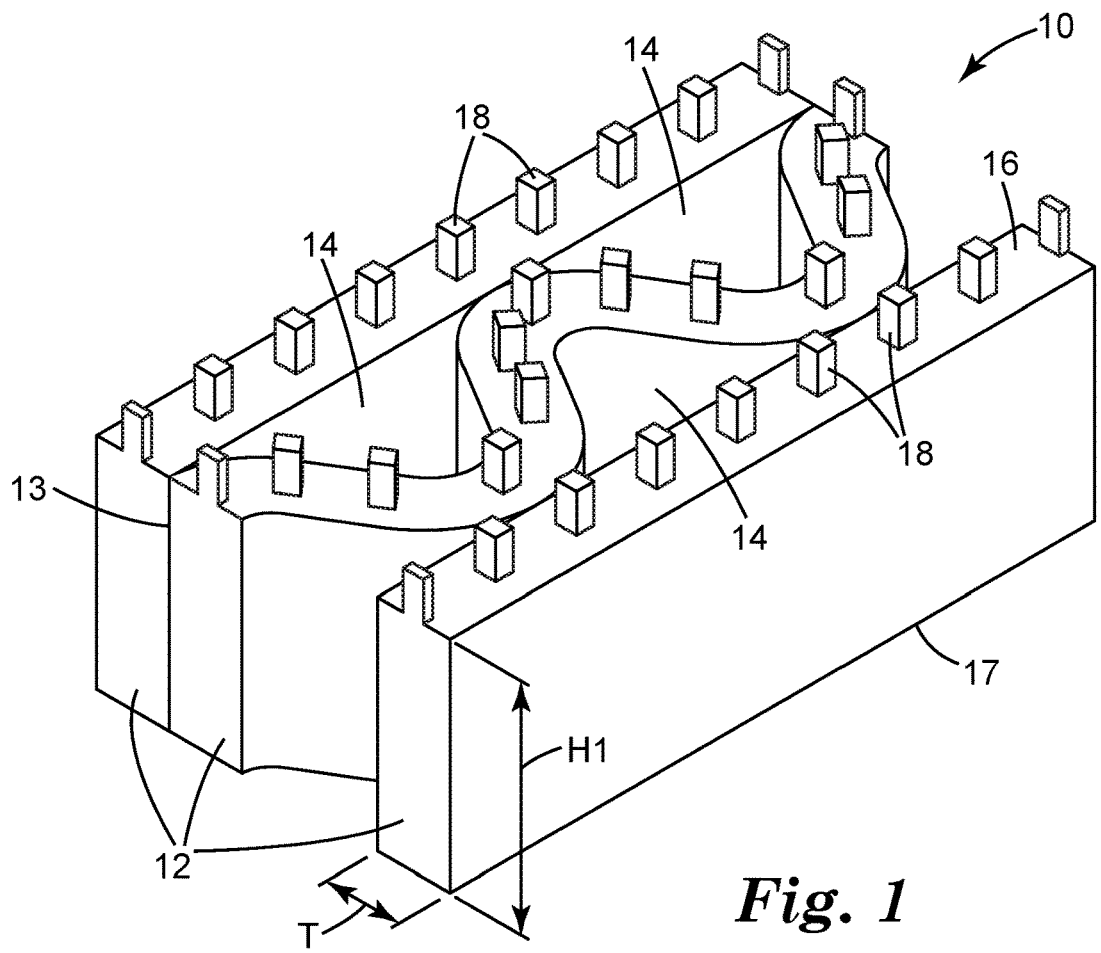
FIG. 1 illustrates an article according to an embodiment of the present invention.

While the above-identified drawings, which may not be drawn to scale, set forth various embodiments of the present disclosure, other embodiments are also contemplated, as noted in the Detailed Description. In all cases, this disclosure describes the presently disclosed invention by way of representation of exemplary embodiments and not by express limitations. It should be understood that numerous other modifications and embodiments can be devised by those skilled in the art, which fall within the scope and spirit of this disclosure.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

As used in this Specification, the recitation of numerical ranges by endpoints includes all numbers subsumed within that range (e.g. 1 to 5 includes 1, 1.5, 2, 2.75, 3, 3.8, 4, and 5, and the like).

Unless otherwise indicated, all numbers expressing quantities or ingredients, measurement of properties and so forth used in the Specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

The article of the present application is well suited to promote tissue growth at the tissue site yet prevent in-growth of new tissue into the article. The article of the present application can help to deliver a significant portion of microstrain to the wound site by the architecture of the article, for example, the surface morphology of the article and thus may allow for lower pressure settings for NPWT to be used (for example, −75 mmHg vs −125 mmHg). This may allow a longer battery life of the NPWT system and the use of smaller pumps for the NPWT.

Referring to FIG. 1, an article 10 according to an embodiment of the present invention includes a network of interconnected polymeric strands, or sheets 12 and a plurality of openings 14 between adjacent polymeric strands. Polymeric strands 12 can be connected at connections 13. Typically, there are a plurality of connections 13 between adjacent strands. Polymeric strands 12 have a tissue contact surface 16 as a first surface and a second surface 17 opposite the first surface. The first surface 16 may include a plurality of features, or protrusions 18 that extend from the first surface 16. In some embodiments, the features 18 do not substantially contact each other (i.e., at least 50 (at least 55, 60, 65, 70, 75, 80, 85, 90, 95, 99, or even 100) percent by number do not contact each other). The openings 14 form or provide open fluid channels from the first surface 16 of the network of polymeric strands to a second surface opposite first surface 16. Through the open fluid channels, openings 14 are typically used to allow reduced pressure applied to a tissue site.

Referring more specifically to FIG. 1, the height, H1, of each polymeric strand 12 may be up to 2000 micrometers, up to 1500 micrometers, up to 1000 micrometers, up to 500 micrometers, or up to 400 micrometers. In some embodiments, the height, H1, of each polymeric strand 12 may be no less than 100 micrometers, no less than 200 micrometers, or no less than 300 micrometers. In some embodiments, the height, H1, of each polymeric strand 12 may be between 100 and 2000 micrometers, between 200 and 1500 micrometers, between 300 and 1000 micrometers, between 300 and 500 micrometers or between 300 and 400 micrometers. In some embodiments, the thickness, T, of each polymeric strand 12 may have an average width up to 500 micrometers, up to 400 micrometers, or up to 250 micrometers. In some embodiments, the thickness, T, of each polymeric strand 12 may have an average width no less than 10 micrometers. In some embodiments, the thickness, T. of each polymeric strand 12 may have an average width in a range from 10 micrometers to 500 micrometers, from 10 micrometers to 400 micrometers, or 10 micrometers to 250 micrometers. In some embodiments, the article comprising interconnected polymeric strands has an average thickness not greater than 5 mm. In one embodiment of the present invention, the height and thickness of the interconnected polymeric strands 12 is uniform for a particular article 10. In other embodiments, the height and thickness of the interconnected polymeric strands 12 may be different. For example, the interconnected polymeric strands 12 having different height. Similarly, thickness of the interconnected polymeric strands 12 may vary. In some, embodiments, the interconnected polymeric strands 12 may have a range of thicknesses, for example, the interconnected polymeric strands 12 tends to be thinnest where it abuts an opening.

In some embodiments, the article comprising interconnected polymeric strands has a thickness up to 2 mm, up to 1 mm, up to 500 micrometers, up to 250 micrometers, up to 100 micrometers, up to 75 micrometers, up to 50 micrometers, or up to 25 micrometers. In some embodiments, the article comprising interconnected polymeric strands has a thickness no less than 10 micrometers. In some embodiments, the article comprising interconnected polymeric strands has a thickness in a range from 10 micrometers to 2 mm, 10 micrometers to 1 mm, 10 micrometers to 750 micrometers, 10 micrometers to 500 micrometers, 10 micrometers to 250 micrometers, 10 micrometers to 100 micrometers, 10 micrometers to 75 micrometers, 10 micrometers to 50 micrometers, or 10 micrometers to 25 micrometers. In some embodiments, the article comprising interconnected polymeric strands has an average thickness in a range from 250 micrometers to 5 mm.

Figure 2:
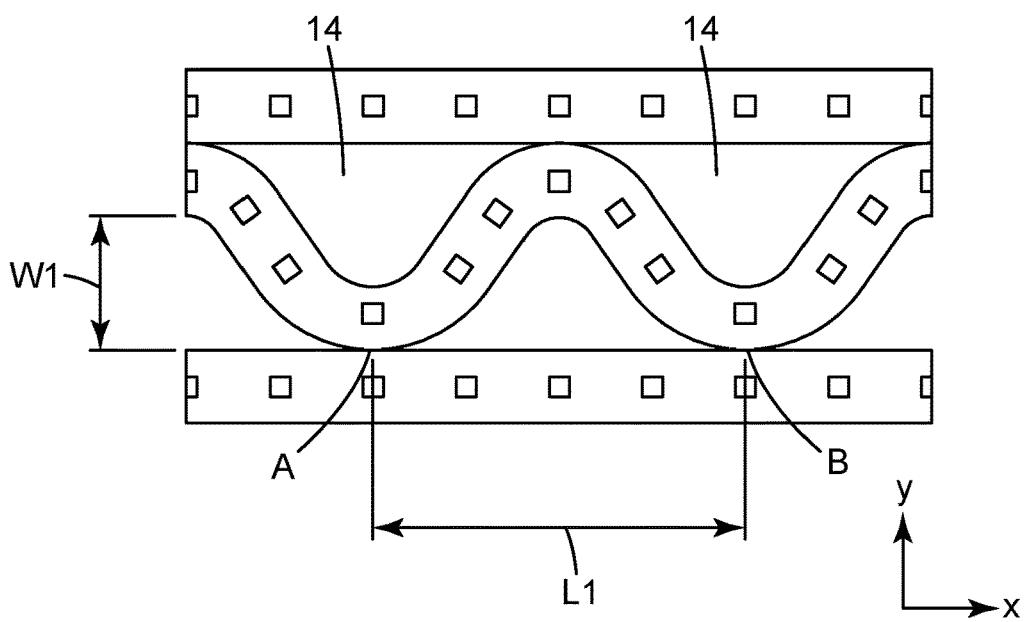
FIG. 2 illustrates a top view of an article according to an embodiment of the present invention.

In some embodiments, at least one of the interconnected polymeric strands 12 may be non-linear. In some embodiments, at least 25% of the interconnected polymeric strands 12 may be non-linear. In some embodiments, at least 50% of the interconnected polymeric strands 12 may be non-linear. In some embodiments, at least 75% of the interconnected polymeric strands 12 may be non-linear. In some embodiments, essentially all the interconnected polymeric strands 12 may be non-linear. In some embodiments, all of the interconnected polymeric strands 12 may be non-linear. In some embodiments, the non-linear polymeric strand may have a shape of a curve. In some embodiments, the non-linear polymeric strand may have a shape of a sinusoidal curve. In some embodiments, the non-linear polymeric strand may have a shape of a sinusoidal curve. In other embodiments, at least one of the interconnected polymeric strands 12 may be linear. In some other embodiments, 25% to 75% of the interconnected polymeric strands 12 may be linear. In some other embodiments, 50% to 75% of the interconnected polymeric strands 12 may be linear. In certain embodiments, the network of interconnected polymeric strands may include alternating non-linear polymeric strands and linear polymeric strands, as shown in FIG. 2. In some embodiments, the interconnected polymeric strands 12 are oriented in the same direction, for example, x direction as illustrated in FIG. 2. In some embodiments, the interconnected polymeric strands 12 do not substantially cross over each other (i.e., at least 50 (at least 55, 60, 65, 70, 75, 80, 85, 90, 95, 99, or even 100) percent by number do not cross over each other).

In some embodiments, aspect ratio (a ratio of the length to the width) of the openings 14 may be greater than 1:1, 1.5:1, 2:1, 3:1 or 5:1. In some embodiments, aspect ratio (a ratio of the length to the width) of the openings 14 may be in a range from 1:1 to 100:1, 1:1 to 75:1, 1:1 to 50:1, 1:1 to 25:1, 2:1 to 100:1 2:1 to 75:1, 2:1 to 50:1, 2:1 to 25:1, or 2:1 to 10:1. The length, L1, of an opening 14 illustrated in FIG. 2 is the longest lateral distance parallel to x direction, for example, the length between connections A and C. If the non-linear polymeric strand has a shape of a sinusoidal curve, the length of the opening 14 equals the wavelength of the sinusoidal curve. The width, W1, of an opening 14 illustrated in FIG. 2 is the longest distance parallel to y direction. If the non-linear polymeric strand has a shape of a sinusoidal curve, the width of the opening 14 equals two times amplification of the sinusoidal curve. Openings 14 of the article may have a range of L1 and W1 values as a result in part of variable spacing of the connections A and B.

In some embodiments, the openings have widths. W1, up to 10 mm, up to 1 mm or up to 0.5 mm. In some embodiments, the openings have widths, W1, at least 5 micrometers or at least 10 micrometers. In some embodiments, the openings have widths, W1, in a range from 5 micrometers to 1 mm or from 10 micrometers to 0.5 mm. In some embodiments, the openings have lengths, L1, up to 10 mm or up to 1 mm. In some embodiments, the openings have lengths, L1, at least 100 micrometers. In some embodiments, the openings have lengths, L1, in a range from 100 micrometers to 10 mm or from 100 micrometers to 1 mm. FIGS. 1 and 2 are idealized illustrations of one embodiment of the present application. In some embodiments, the openings 14 may have irregularly formed perimeters. This can mean that the openings have irregular shapes (that is, no lines of symmetry). They may have edges that are not smooth (e.g., jagged or feathery edges). Irregularly formed openings can also have a variety of thicknesses of the polymeric strands surrounding the openings.

In some embodiments, openings 14 may have any suitable shape, for example, a shape selected from shapes of ellipse, oval, pointed oval (or lens), diamond, ½ ellipse, ½ oval, ½ lens, triangle, etc. In some embodiments, the openings of the mechanical fastening nets described herein have at least two pointed ends. In some embodiments, at least some of the openings are elongated with two pointed ends. In some embodiments, at least some of the openings are elongated with two opposed pointed ends. In some embodiments, at least some of the openings are ovals.

In some embodiments, the article described herein have a total open area for each of the first and second, generally opposed surfaces of not greater than 50 (in some embodiments, not greater than 45, 40, 35, 30, 25, 20, 15, 10, 5, 4 3, 2, 1, 0.75, 0.5, 0.25, or even not greater than 0.1) percent of the total area of the respective surface. In some embodiments, for at least a majority of the openings of the article described herein, the maximum area of each opening is not greater than is 5 (in some embodiments, not greater than 2.5, 2, 1, 0.5, 0.1, 0.05, 0.01, 0.075, or even not greater than 0.005) mm². Individual openings range from 0.005 mm to 5 mm. In some embodiments, the article according to the present disclosure have in a range from 50,000 to 6,000,000 (in some embodiments, 100,000 to 6,000,000, 500,000 to, 6,000,000, or even 1.000.000 to 6,000,000) openings/m².

In some embodiments, the tensile strength of the article parallel to x direction may be greater than the tensile strength of the article parallel to y direction. Therefore, the article is easier to be stretched in y direction than in x direction. In some embodiments, the tensile strength of the article parallel to x direction is at least 2.23 MPa, at least 2.25 MPa, at least 2.5 MPa or at least 3.0 MPa. In some embodiments, the tensile strength of the article parallel to x direction is up to 5.42 MPa, up to 5.3 MPa, up to 5.0 MPa, or up to 4.5 MPa. In some embodiments, the tensile strength of the article parallel to x direction is from 2.23 MPa to 5.42 MPa, from 2.5 MPa to 5.0 MPa or from 3.0 MPa to 4.5 MPa. The Young's modulus of the article is up to 10.6 MPa, up to 10.0 MPa, up to 9.0 MPa, or up to 8.0 MPa. The Young's modulus of the article is at least 3.85 MPa, at least 4.0 MPa has a range from 3.85 MPa to 10.6 MPa in a direction parallel to x direction.

The shape, sizing, and spacing of the features 18 may vary depending upon the particular tissue site being treated, the type of material from which the features 18 and polymeric strands are made, and the amount of reduced pressure being applied to the tissue site. For example, for tissue sites that are highly exudating, it may be advantageous to position the protrusions farther apart or reduce the density of features on the first surface to maintain adequate distribution channels between the features 18. In one embodiment of the present invention, the shape, sizing and spacing of the features 18 is uniform for a particular article 10. In other embodiments, the shape, sizing, and spacing of the features 18 may be different. For example, features 18 having different cross-sectional shapes may be disposed on the first surface. Similarly, the sizing and spacing of the features 18 may vary to supply selected portions of the tissue site with different (more or less) reduced pressure and different flow rate for exudates withdrawn.

Figure 3:
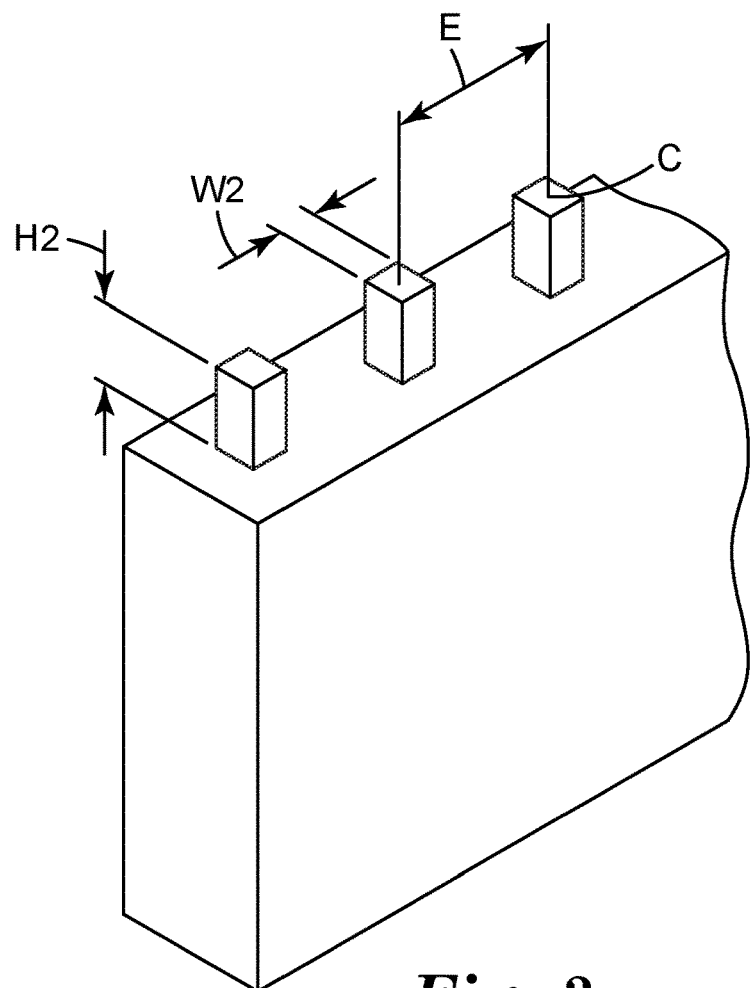
FIG. 3 illustrates the shape of the features of the article according to an embodiment of the present invention.

Referring more specifically to FIG. 3, the height, H2, of the features 18 may be up to 1000 micrometers, up to 500 micrometers or up to 450 micrometers. In some embodiments, the height, H2, of the features 18 may be at least 100 micrometers or at least 200 micrometers. In some embodiments, the height, H2, of the features 18 may be between 100 and 1000 micrometers, between 200 and 500 micrometers or between 200 and 450 micrometers. The width, W2, of each feature may be up to 1000 micrometers, up to 900 micrometers, up to 800 micrometers, up to 700 micrometers or up to 600 micrometers. In some embodiments, the width, W2, of each feature may be at least 10 micrometers, at least 100 micrometers, at least 200 micrometers, at least 300 micrometers or at least 400 micrometers. In some embodiments, the width, W2, of each feature may be between 10 and 1000 micrometers, between 100 and 900 micrometers, between 200 and 800 micrometers, between 300 and 700 micrometers, or between 400 and 600 micrometers. In some embodiments, the width, W2, of each feature may be 500 micrometers. The width of the features 18 illustrated in FIG. 3 is an edge length of the square since the cross-sectional shape of each features 18 is square. If the features 18 are circular in cross-sectional shape, the width of the features 18 equals the diameter since the cross-sectional shape of each feature 18 is circular. For other cross-sectional shapes, the width is the average of the longest lateral distance through the centroid, C, of the cross section and the shortest lateral distance through the centroid of the cross section. It is generally preferred that the height of the features 18 be no more than the width of the features 18. More specifically, the ratio of height to width, H2:W2 of the features 18, should be no more than 1:1. When the ratio of height to width, H2:W2 of the features 18, is more than 1:1, the features 18 is more prone to fall over the openings 14, thus reducing the fluid flow through the openings 14. The lateral, center-to-center spacing, E, between each feature 18 may be between 0.1 and 2.0 millimeters, between 0.5 and 1.5 millimeters or between 0.7 and 1.3 millimeters. The spacing of the features 18 create distribution channels through which reduced pressure may be delivered to the tissue site and exudates withdrawn from the tissue site. The density of features on the first surface may be less than 1,000/square inch to facilitate reduced pressure delivered to the tissue site and exudates withdrawn from the tissue site. In some embodiments, the density of features on the first surface may be less than 1,000/square inch, less than 900/square inch, less than 800/square inch, less than 700/square inch, less than 600/square inch, or less than 500/square inch. In some embodiments, the number of features in the article can be greater than the number of openings. For example, the ratio of the number of features to the number of openings can be more than 1, 1.5, 2, 2.5, 3, 4, 5, or 10. In some embodiments, the article of the present disclosure can be a mechanical fastening net or a mechanical fastening sheet with features.

In some embodiments, features 18 are oriented along the interconnected polymeric strands 12 as illustrated in FIG. 1. In other embodiments, features 48 are oriented in substantially same orientation, for example x direction, as illustrated in FIG. 2.

The presence and sizing of the features 18 allow the features 18 to distribute reduced pressure to the tissue site, but prevent new tissue that grows at the tissue site from attaching to the features 18 or growing into the spacing between features 18. While new tissue growth may wrap around some of the features 18, the new tissue is not capable of securing itself to the features 18 since the base of each features is anchored to the first surface 16.

In addition to distributing reduced pressure to the tissue site, the article 10 also serves to impart stresses and strains to the tissue site similar to those seen with cellular foam that traditionally has been used in reduced pressure systems.

Other materials sometimes used in reduced pressure systems, such as gauze, do not have this effect on tissue. Unbound by the theory, the stresses and strains created by the article 10 are believed to cause micro-deformation of existing tissues and plays a significant role in the generation of new tissues at the tissue site. The amount of stress and strain imparted to a tissue site is determined by the amount of reduced pressure supplied to the tissue site and the surface morphology of the article that contacts the tissue site. As reduced pressure is applied, portions of the tissue site are pulled against the article 10, and more particularly against the features 18, which results in the development of stresses and strains within the tissue. In some embodiments, the article of the present disclosure can be a mechanical fastening net or a mechanical fastening sheet with features.

Figure 4:
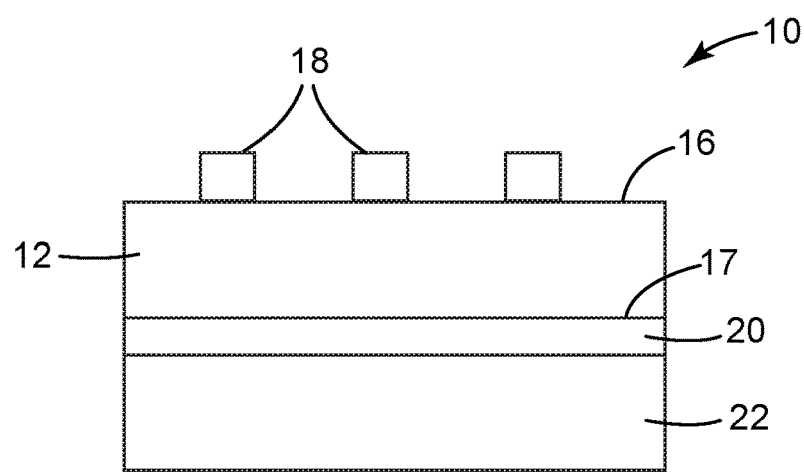
FIG. 4 illustrates a schematic cross-section side view of an article according to an embodiment of the present invention.

Referring to FIG. 4, in some embodiments, the article 10 may further include an adhesive layer 20 in contact with the second surface 17 of the interconnected polymeric strands 12. Suitable adhesive for use in the adhesive layer 20 of the article 10 can include any adhesive that provides acceptable adhesion to skin and is acceptable for use on skin (e.g., the adhesive should preferably be non-irritating and non-sensitizing). Suitable adhesives can be pressure sensitive and in certain embodiments have a relatively high moisture vapor transmission rate to allow for moisture evaporation. Suitable pressure sensitive adhesives include those based on acrylates, urethane, hyrdogels, hydrocolloids, block copolymers, silicones, rubber based adhesives (including natural rubber, polyisoprene, polyisobutylene, butyl rubber etc.) as well as combinations of these adhesives. The adhesive component may contain tackifiers, plasticizers, rheology modifiers as well as active components including for example an antimicrobial agent. Suitable adhesive can include those described in U.S. Pat. Nos. 3,389,827; 4,112,213; 4,310,509; 4,323,557; 4,595,001; 4,737,410; 6,994,904 and International Publication Nos. WO 2010/056541; WO 2010/056543 and WO 2014/149718, the disclosures of which are hereby incorporated by reference.

The article 10 may further include a filler 22 in contact with the adhesive layer 20, the adhesive layer 20 in between the network of interconnected polymeric strands 12 and the filler 22. The filler is useful to allow for fluid transport under vacuum into the filler, but with the contact layer providing an interface between the tissue and the filler. Representative filler may include non-woven and woven fibrous webs, knits, films, foams polymeric films and other familiar filler materials. The features 18 and interconnected polymeric strands serve as a barrier to new tissue growth entering pores of the filler 22. In some embodiments, the filler can be a foam. In some embodiments, the filler can be a cellular foam. In some embodiments, the filler can be an open cellular foam. In some embodiments, the filler can be a closed cellular foam. In some embodiments, the filler can comprises an elastomeric polyurethane, polyester, or polyether block amide foam or film.

The article 10 may further include an occlusive layer 22 to cover the filler, adhesive layer and the contact layer. The occlusive layers are useful to provide an impermeable barrier to the passage of liquids and at least some gases and help to deliver and distribute reduced pressure to the article 10. Representative barriers may include non-woven and woven fibrous webs, knits, films, foams polymeric films and other familiar backing materials. In some embodiments, a transparent occlusive layer is desirable to allow for viewing of the underlying subjects. Suitable occlusive layers may include those described in International Publication No. WO 2014/149718, the disclosures of which are hereby incorporated by reference.

In one embodiment, the occlusive layer has high moisture vapor permeability, but generally impermeable to liquid water so that microbes and other contaminants are sealed out from the area under the article. One example of a suitable material is a high moisture vapor permeable film such as described in U.S. Pat. Nos. 3,645,835 and 4,595,001, the disclosures of which are herein incorporated by reference. In one embodiment, the occlusive layer can be an elastomeric polyurethane, polyester, or polyether block amide films. These films combine the desirable properties of resiliency, elasticity, high moisture vapor permeability, and transparency. A description of this characteristic of occlusive layers can be found in issued U.S. Pat. Nos. 5,088,483 and 5,160,315, the disclosures of which are hereby incorporated by reference.

Commercially available examples of potentially suitable materials for the occlusive layer may include the thin polymeric film sold under the trade names TEGADERM (3M Company), OPSITE (Smith & Nephew), etc. Because fluids may be actively removed from the sealed environments defined by the article, a relatively high moisture vapor permeable occlusive layer may not be required. As a result, some other potentially useful materials for the occlusive layer may include, e.g., metallocene polyolefins and SBS and SIS block copolymer materials could be used.

Regardless, however, it may be desirable that the occlusive layer be kept relatively thin to, e.g., improve conformability. For example, the occlusive layer may be formed of polymeric films with a thickness of 200 micrometers or less, or 100 micrometers or less, 50 micrometers or less, or 25 micrometers or less.

Figure 5:
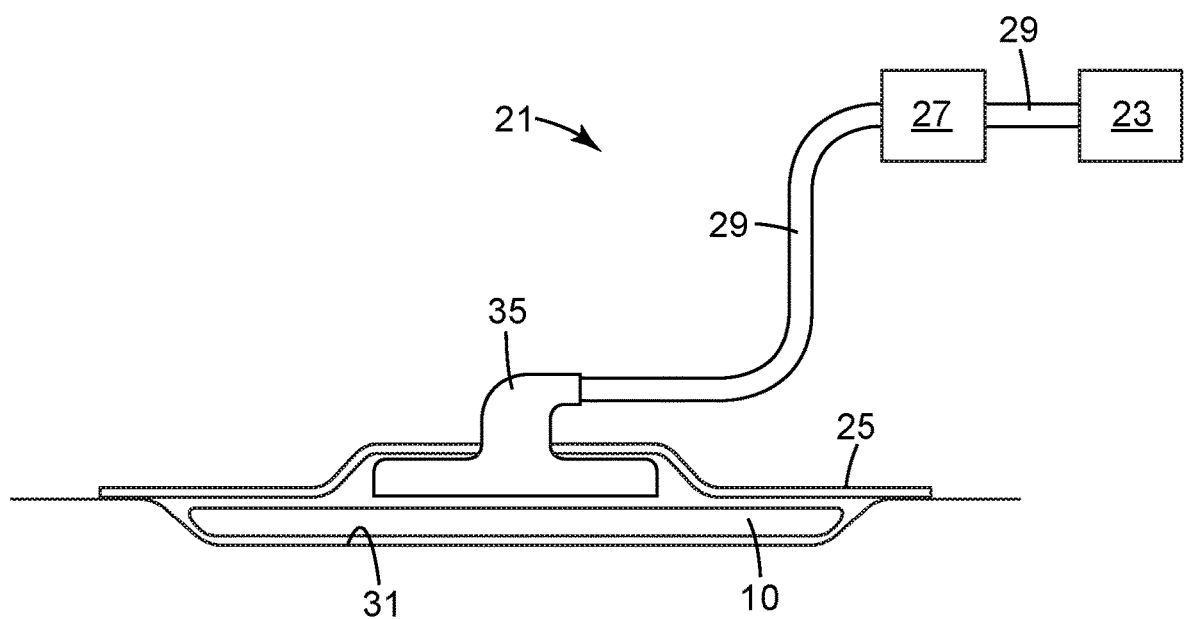
FIG. 5 illustrates a reduced pressure treatment system according to an embodiment of the present invention.

Referring to FIG. 5, a reduced pressure treatment system 21 according to an embodiment of the present invention includes a reduced pressure dressing, or article 10 fluidly connected to a reduced pressure conduit 29. The reduced pressure conduit 29 is fluidly connected to a reduced pressure source 23 such as a vacuum pump or another source of suction. The article 10 is placed against a tissue site 31 of a patient and is used to distribute a reduced pressure provided by the reduced pressure source 23. Typically, reduced pressure is maintained at the tissue site by placing an impermeable or semi-permeable cover 25 over the article 10 and the tissue site 31. The reduced pressure also serves to draw wound exudates and other fluids from the tissue site 31. A canister 27 may be fluidly connected to the reduced pressure conduit 29 and disposed between the article 10 and the reduced pressure source 23 to collect the fluids drawn from the tissue site 31. A distribution adapter 35 may be connected to the reduced pressure conduit 29 and positioned on the article 10 to aid in distributing the reduced pressure to the article 10.

In some embodiments, the interconnected polymeric strands 12 can include an elastomeric polymer. Elastomeric polymer can be any suitable elastomeric polymer, including but not limited to polyolefins and polyurethanes. In some embodiments, elastomeric polymer can be a medical grade material that is relatively impermeable to fluid flow. Alternatively, elastomeric polymer can be a semi-permeable material that allows select fluids or amounts of fluids to pass. In some embodiments, the interconnected polymeric strands 12 are formed from the same material as the features 18. In some embodiments, the interconnected polymeric strands 12 can be formed from a different material as the features 18.

In some embodiments, the composition of interconnected polymeric strands 12 may be formed from different materials.

Some embodiments of the present wound-treatment methods can include positioning the article of present disclosure on a wound of a patient and applying a reduced pressure to the wound through the article (e.g., through the openings). Some embodiments further comprise: coupling a drape to skin adjacent the wound such that the drape covers the article and the wound, and forms a space between the drape and the wound. In some embodiments, positioning the article on the wound can include placing the article over the wound with the features on the first surface facing the wound. In some embodiments, applying the reduced pressure to the wound comprises activating a vacuum source (e.g., reduced pressure source 23 of FIG. 5) that is coupled to the article. Some embodiments comprise: delivering a fluid to the wound through the article. In some embodiments, delivering a fluid comprises activating a fluid source that is coupled to the article.

The following embodiments are intended to be illustrative of the present disclosure and not limiting.

EMBODIMENTS

Embodiment 1 is an article, comprising: a network of interconnected polymeric strands; wherein each of the interconnected polymeric strands has a first surface adapted to contact a tissue site and a second surface opposite the first surface; wherein at least one of the interconnected polymeric strand has a plurality of features extending from the first surface of the interconnected polymeric strands; wherein at least one of the interconnected polymeric strands is non-linear; a plurality of openings between adjacent interconnected polymeric strands; an adhesive layer in contact with the second surface of the interconnected polymeric strands; and a filler in contact with the adhesive layer, the adhesive layer in between the network of interconnected polymeric strands and the filler; wherein the article is a negative pressure wound therapy article.

Embodiment 2 is the article of embodiment 1, wherein at least one of the interconnected polymeric strands is linear.

Embodiment 3 is the article of any one of embodiments 1 to 2, wherein the network comprises alternating non-linear polymeric strands and linear polymeric strands.

Embodiment 4 is the article of any one of embodiments 1 to 3, wherein the non-linear polymeric strand has a sinusoidal curve.

Embodiment 5 is the article of any one of embodiments 1 to 4, wherein the filler comprises a polyurethane foam.

Embodiment 6 is the article of any one of embodiments 1 to 5, wherein the tensile strength of the article parallel to x direction is more than 2.23 Mpa.

Embodiment 7 is the article of any one of embodiments 1 to 6, wherein the polymeric strands comprises an elastomeric polymer.

Embodiment 8 is the article of embodiment 7, wherein the elastomeric polymer is selected from polyolefins or polyurethanes.

Embodiment 9 is the article of any one of embodiments 1 to 8, wherein the features have a height of 100 µm to 1000 µm.

Embodiment 10 is the article of any one of embodiments 1 to 9, wherein the features have a width of 10 µm to 1000 µm.

Embodiment 11 is the article of any one of embodiments 1 to 10, wherein a ratio of the height to width of the features is no more than 1:1

Embodiment 12 is the article of any one of embodiments 1 to 11, wherein the density of features extending from the first surface is less than 1,000/square inch.

Embodiment 13 is the article of any one of embodiments 1 to 12, wherein aspect ratio of the openings is greater than 1:1.

Embodiment 14 is the article of any one of embodiments 1 to 13, wherein essentially all the interconnected polymeric strands are non-linear.

Embodiment 15 is a system, comprising: the article of any one of embodiments 1 to 14; and a reduced pressure source connected to article to deliver the reduced pressure through the opening, between the features, and to the tissue site.

Embodiment 16 is a method, comprising: providing the article of any one of embodiments 1 to 14; and positioning the article on a wound.

Embodiment 17 is the method of embodiment 16, further comprising coupling a reduced pressure source to the article.

Embodiment 18 is the method of embodiment 16, further comprising applying a reduced pressure to the wound through the article.

Embodiment 19 is the method of embodiment 18, wherein applying the reduced pressure to the wound comprises activating the reduced pressure source coupled to the article.

Embodiment 20 is the method of any one of embodiments 16 to 19, wherein positioning the article on the wound comprises placing the article over the wound with the features on the first surface facing the wound.

The following working examples are intended to be illustrative of the present disclosure and not limiting.

EXAMPLES

Example 1

A polyolefin net was prepared using ENGAGE 8200 polyolefin elastomer (obtained from the Dow Chemical Company, Midland, Mich.) according to the methods described in United States Patent Application 2014/0234606 (Ausen), herein incorporated by reference in its entirety. The resulting net material had strand width ranges of about 0.42-0.83 mm, pore width ranges of about 0.15-0.57 mm, pore length ranges of about 1.5-2.1 mm, and a thickness range of about 0.75-1.24 mm. The net sample was embossed by stacking from top to bottom a steel plate, a square pattern polypropylene film that served as the mold (inner dimension of a square being approximately 0.5 mm), the polyolefin net sample, a release liner, and a second steel plate. The stack was placed in a Carver Auto Series NE Automatic Hydraulic Press (Model 3895.4NE1000, Carver Inc., Wabasha, Ind.) with the bottom platen of the press set at 21° C. and the top platen set at 121° C. The press was closed and the sample was held at a set force of 794 kg for two minutes, followed by a cool down period of four minutes to 65.5° C. The press was opened and the embossed sample was removed from the press. The resulting embossed article had a base thickness range of about 0.56-0.65 mm; strand width ranges of about 0.45-0.50 mm; openings with width ranges of about 0.13-0.37 mm and length ranges of about 0.87-1.10 mm; features with width at base of about 0.5 mm and height ranges of about 0.29-0.50 mm; and feature spacing ranges of about 0.77-0.94 mm.

An 18 cm by 12.5 cm section of the embossed article was prepared and the surface of the article without features was modified by corona treatment for about one minute using a hand-held unit with rastering motion (Model BD-20 Laboratory Corona Treater, Electro-Technic Products Company, Chicago, Ill.). One surface of an 18 cm by 12.5 cm (12 mm thick) pad of GRANUFOAM polyurethane foam (V.A.C. Granufoam Dressing Medium, KCl Incorporated, San Antonio, Tex.) was also modified using the corona treatment procedure described above.

An 18 cm by 12.5 cm section of 3M #2477 Double-Coated TPE Silicone/Acrylic adhesive tape (3M Company, Maplewood, Minn.) that had been perforated (1 mm diameter perforations patterned 3 mm center-to-center) was prepared. The paper release liner was removed and the exposed adhesive surface was heated for 10-20 seconds with hot air from an electric heat gun. The adhesive tape was edge aligned and applied to the corona treated surface of the foam pad. Next, the plastic release liner was removed from the tape and the corona treated surface of the embossed article was edge aligned and applied to the exposed adhesive surface. Hand pressure was applied to the resulting laminate for 5-10 seconds followed by placement of a 1.28 Kg weight on the laminate overnight. The weight was removed to provide the finished laminated article.

Example 2

A double sided acrylic adhesive transfer tape (3M 300LSE tape #9472LE, 3M Company) was perforated through all layers in a repeating hexagonal pattern with 5 mm diameter perforations spaced 1 cm center-to-center. A 2.5 cm by 2.5 cm section of the embossed article of Example 1 was prepared and the surface of the article without features was modified by corona treatment for 15-20 seconds using a hand-held unit with rastering motion (Model BD-20 Laboratory Corona Treater). One surface of a 2.5 cm by 2.5 cm (12 mm thick) pad of GRANUFOAM polyurethane foam (V.A.C. Granufoam Dressing Medium) was also modified using the corona treatment procedure described above.

One of the release liners was removed from a 2.5 cm by 2.5 cm section the double sided adhesive transfer tape and the exposed adhesive surface was heated for 10-20 seconds with hot air from an electric heat gun. The adhesive was edge aligned and applied to the corona treated surface of the foam pad. Next, the second release liner was removed and the corona treated surface of the embossed article was edge aligned and applied to the exposed adhesive surface. Hand pressure was applied to the resulting laminate for a few seconds followed by placement of a 0.46 Kg weight on the laminate overnight. The weight was removed to provide the finished laminated article.

Example 3. Determination of Fibroblast Proliferation Using an In Vitro Cell Culture Device A cell culture device having a lower base unit, an o-ring seal in the lower base unit, an upper base unit, a cell culture insert for growing cell cultures, a flexible sealing member, a guide tube with two open ends, a support bracket, a vacuum conduit, a media conduit, and attachment screws was used. The lower base unit had a circular interior cavity. The upper base unit was placed on top of lower base unit. The upper base unit had an open, interior channel that was dimensioned to align with the cavity opening of the lower base unit. The o-ring seal was pressed into a recess in the wall of the lower base unit. The cell culture insert was placed in the channel and pressed into the sealing element. The seal engaged the sidewalls of the cell culture insert to create a substantially air-tight seal. The base of the cell culture insert contained a permeable membrane. An upper assembly comprising a flexible sealing member, guide tube, and support bracket was placed on top of the upper base unit so that the guide tube was in fluid communication with the cell culture insert. The components of the device were then secured together with screws. The vacuum conduit was attached at one end to the guide tube and at the other end to a vacuum pump. The media conduit was connected at one end to a reservoir containing media and at the other end to the internal cavity of the lower base unit (near the floor). The media was pumped from the reservoir so that it flowed into the cavity of the lower base unit and then passed through the permeable membrane of the insert to the gel matrix.

Fibroblasts were encapsulated in a fibrin gel matrix (clot) to simulate a component of the wound healing environment. The matrix was prepared by the following three step procedure. First, a layer of fibrin gel was prepared and applied to the internal surface of the permeable membrane (24 mm diameter with 1 micron pore size) in a MILLICELL hanging cell culture insert (obtained from EMD Millipore, Billerica, Mass.) by combining 1 mL of human fibrinogen (concentration of 9.8 mg per mL of porcine plasma) with 0.25 mL of thrombin (concentration of 500-1100 units per mL of porcine plasma) (human fibrinogen obtained from Sigma-Aldrich Corporation, St. Louis, Mo.; thrombin obtained from BioPharm Laboratories, Bluffdale, Utah; porcine plasma obtained from Lampire Biological Lab, Piphersville, Pa.). This layer was covered with a layer of about 50,000 fibroblasts (obtained from Invitrogen Corporation, Carlsbad, Calif.). The fibroblast layer was then covered with a third (or top layer) of fibrin gel prepared in the same manner as for the first layer. Following encapsulation in the gel, the fibroblasts were grown in an incubator at 37° C. for two days.

In the cell proliferation assay, the finished article of Example 1 (10 cm by 12.5 cm) was placed over the top layer of the matrix with the surface of the article containing the feature elements facing and in contact with the gel matrix. Fibroblast Culture Medium 106 (obtained from Invitrogen Corporation) was continuously supplied to the gel matrix by means of a peristaltic pump. Negative pressure (−125 mm Hg) was applied to the device for 48 hours at 37° C. The device was then dismantled and the fibroblast sample was evaluated for cell proliferation using an XTT colorimetric assay kit (obtained from Invitrogen Corporation) with the absorbance measurements taken at 570 nm using a SpectraMax M5 plate reader (Molecular Devices, Sunnyvale, Calif.). The level of fibroblast cell proliferation for the example was compared to a control experiment. In the control experiment, the same procedure was used except that the finished article of Example 1 was not added to the apparatus and negative pressure was not applied for the 48 hour test period. In Table 1, the mean percent increase in recorded absorbance for the example compared to the control is reported (3 replicates).

TABLE 1

| Cell Proliferation Assay | |
| --- | --- |
| Embossed Article | Percent Increase in Absorbance as Compared to Control |
| Example 1 | 11.6 |

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. An article, comprising:
   a network of interconnected polymeric strands; wherein each of the interconnected polymeric strands has a first surface adapted to contact a tissue site and a second surface opposite the first surface; wherein at least one of the interconnected polymeric strand has a plurality of features extending from the first surface of the interconnected polymeric strands; wherein at least one of the interconnected polymeric strands is non-linear;
   a plurality of openings between adjacent interconnected polymeric strands;
   an adhesive layer in contact with the second surface of the interconnected polymeric strands; and
   a filler in contact with the adhesive layer, the adhesive layer in between the network of interconnected polymeric strands and the filler;
   wherein the article is a negative pressure wound therapy article.

2. The article of claim 1, wherein at least one of the interconnected polymeric strands is linear.

3. The article of claim 1, wherein the network comprises alternating non-linear polymeric strands and linear polymeric strands.

4. The article of claim 1, wherein the non-linear polymeric strand has a sinusoidal curve.

5. The article of claim 1, wherein the filler comprises a polyurethane foam.

6. The article of claim 1, wherein the tensile strength of the article parallel to x direction is more than 2.23 Mpa.

7. The article of claim 1, wherein the polymeric strands comprises an elastomeric polymer.

8. The article of claim 7, wherein the elastomeric polymer is selected from polyolefins or polyurethanes.

9. The article of claim 1, wherein the features have a height of 100 μm to 1000 μm.

10. The article of claim 1, wherein the features have a width of 10 μm to 1000 μm.

11. The article of claim 1, wherein a ratio of the height to width of the features is no more than 1:1.

12. The article of claim 1, wherein the density of features extending from the first surface is less than 1,000/square inch.

13. The article of claim 1, wherein aspect ratio of the openings is greater than 1:1.

14. The article of claim 1, wherein essentially all the interconnected polymeric strands are non-linear.

15. A system, comprising:
    the article of claim 1; and
    a reduced pressure source connected to article to deliver the reduced pressure through the opening, between the features, and to the tissue site.

16. A method, comprising:
    providing the article of claim 1; and
    positioning the article on a wound.

17. The method of claim 16, further comprising coupling a reduced pressure source to the article.

18. The method of claim 16, further comprising applying a reduced pressure to the wound through the article.

19. The method of claim 18, wherein applying the reduced pressure to the wound comprises activating the reduced pressure source coupled to the article.

20. The method of claim 16, wherein positioning the article on the wound comprises placing the article over the wound with the features on the first surface facing the wound.

* * * * *